US00PP36786P2

(12) United States Plant Patent
Dirr et al.

(10) Patent No.: US PP36,786 P2
(45) Date of Patent: Jul. 1, 2025

(54) ***DISTYLIUM* PLANT NAMED 'CG-46-22'**

(50) Latin Name: ***Distylium* spp. hybrid**
Varietal Denomination: CG-46-22

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/799,876

(22) Filed: Aug. 9, 2024

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

PUBLICATIONS

Dirr, *Distylium*: The Best New Plant You've Never Heard of, Grower Talks 2015, retreived on Nov. 13, 2024 at https://www.growertalks.com/Article/?articleid=21697, 4pp. (Year: 2015).*

* cited by examiner

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Distylium* plant named 'CG-46-22', characterized by its compact, layered (branches uniformly stacked), mounding habit; distinctive greyed-purple new foliage color and lanceolate, olive-green mature foliage. Plants have a low temperature tolerance within USDA Zones 6-9 and are tolerant of high temperatures to at least 95° F. The new variety is a *Distylium*, typically for ornamental garden use.

3 Drawing Sheets

Genus and species of plant claimed: *Distylium* spp. hybrid.

Variety denomination: 'CG-46-22'.

BACKGROUND OF THE INVENTION

The present invention relates to a new and distinct cultivar of *Distylium* plant, botanically known as *Distylium* hybrid, a member of the Hamamelidaceae family, and hereinafter referred to by the cultivar name 'CG-46-22'.

'CG-46-22' originated as an open-pollinated seedling from seed collected from *Distylium* hybrid 'PIIDIST-V', U.S. Plant Pat. No. 27,631, growing in Watkinsville, Georgia. 'CG-46-22' is a *Distylium* spp. hybrid (*Distylium myricoides* x *D. racemosum*) selected in 2022 by the inventors in a cultivated environment in Watkinsville, GA.

Asexual reproduction of 'CG-46-22' was first performed by stem cuttings in 2022 has shown that all the unique features of 'CG-46-22', as herein described, are stable and reproduced true-to-type through successive generations of such asexual propagation. First propagation took place at research nursery in Watkinsville, Georgia.

SUMMARY OF THE INVENTION

'CG-46-22' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'CG-46-22' from all other varieties in commerce known to the inventor:

1. Compact, layered (branches uniformly stacked), and mounding growth habit.
2. Greyed-Purple new growth.
3. Lanceolate, olive-green foliage on mature growth.
4. Low temperature tolerance within USDA Zones 6-9. High temperature tolerance to at least 95° F.

PARENTAL COMPARISON

Plants of the new cultivar 'CG-46-22' are comparable to the seed parent in most horticultural characteristics. However, the new variety 'CG-46-22' differs in the following:

1. New growth of 'CG-46-22' is Greyed-Purple, whereas the new growth of the seed parent is a lighter red.
2. Mature growth of 'CG-46-22' olive-green, whereas the mature growth of the seed parent is blue-green.
3. Plants of 'CG-46-22' are overall larger than plants of the seed parent.

COMMERCIAL COMPARISONS

Plants of the new cultivar 'CG-46-22' can be compared to the commercial cultivar 'PIIDIST-IV', U.S. Plant Pat. No. 25,984, in most horticultural characteristics. However, the new variety 'CG-46-22' differs in the following:

1. Plants of 'CG-46-22' have a compact, layered, mounding habit, whereas plants of this comparator have an upright habit.

2. New growth of 'CG-46-22' is Greyed-Purple, whereas the new growth of this comparator is red.
3. Mature growth of 'CG-46-22' olive-green, whereas the mature growth of this comparator is dark green.

Plants of the new cultivar 'CG-46-22' can be compared to the commercial cultivar 'PIIDIST III', U.S. Plant Pat. No. 25,304, in most horticultural characteristics. However, the new variety 'CG-46-22' differs in the following:

1. Plants of 'CG-46-22' have shown more cold-hardiness than plants of this comparator.
2. New growth of 'CG-46-22' is Greyed-Purple, whereas the new growth of this comparator is bronze-purple.
3. Mature growth of 'CG-46-22' olive-green, whereas the mature growth of this comparator is dark bluish-green.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Distylium*.

DETAILED BOTANICAL DESCRIPTION

Figure 1:
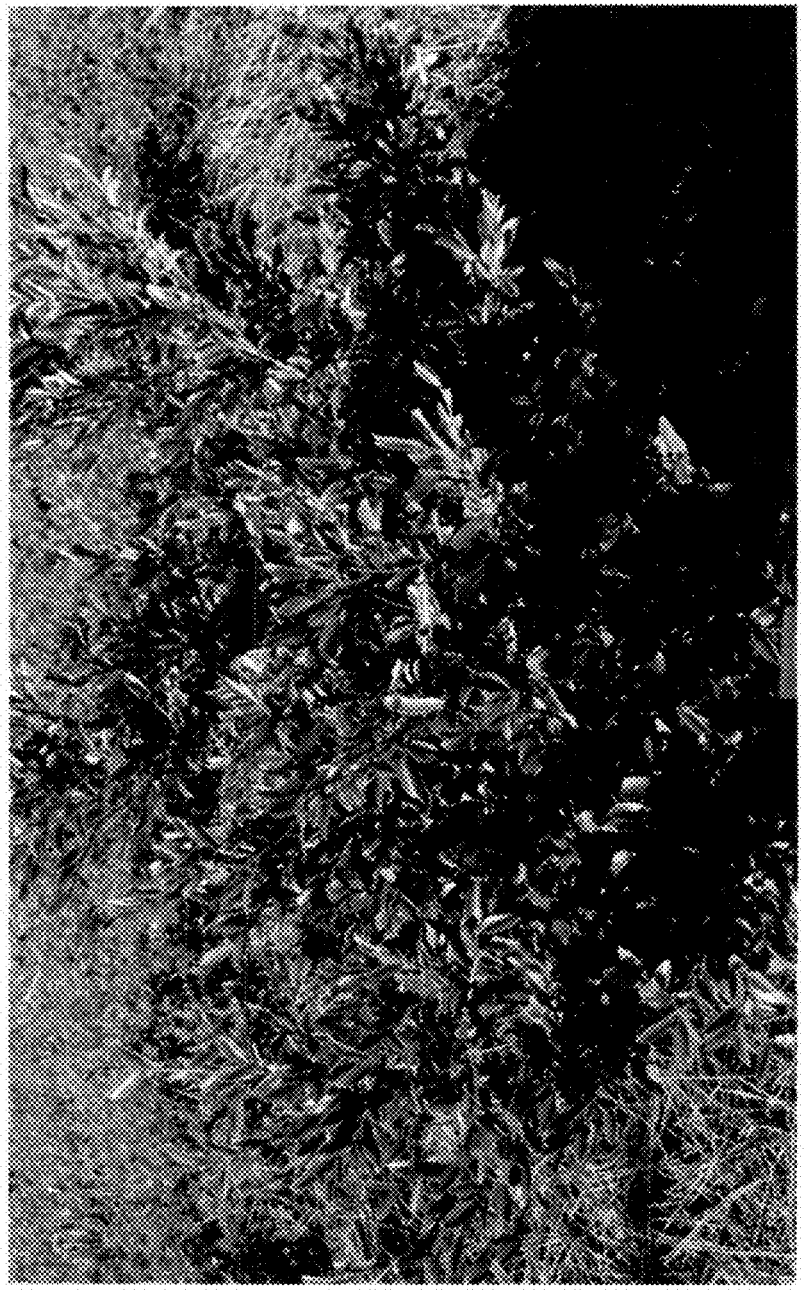
FIG. 1 illustrates the overall appearance and growth habit of a two-year-old 'CG-46-22' plant in the ground.
Figure 2:
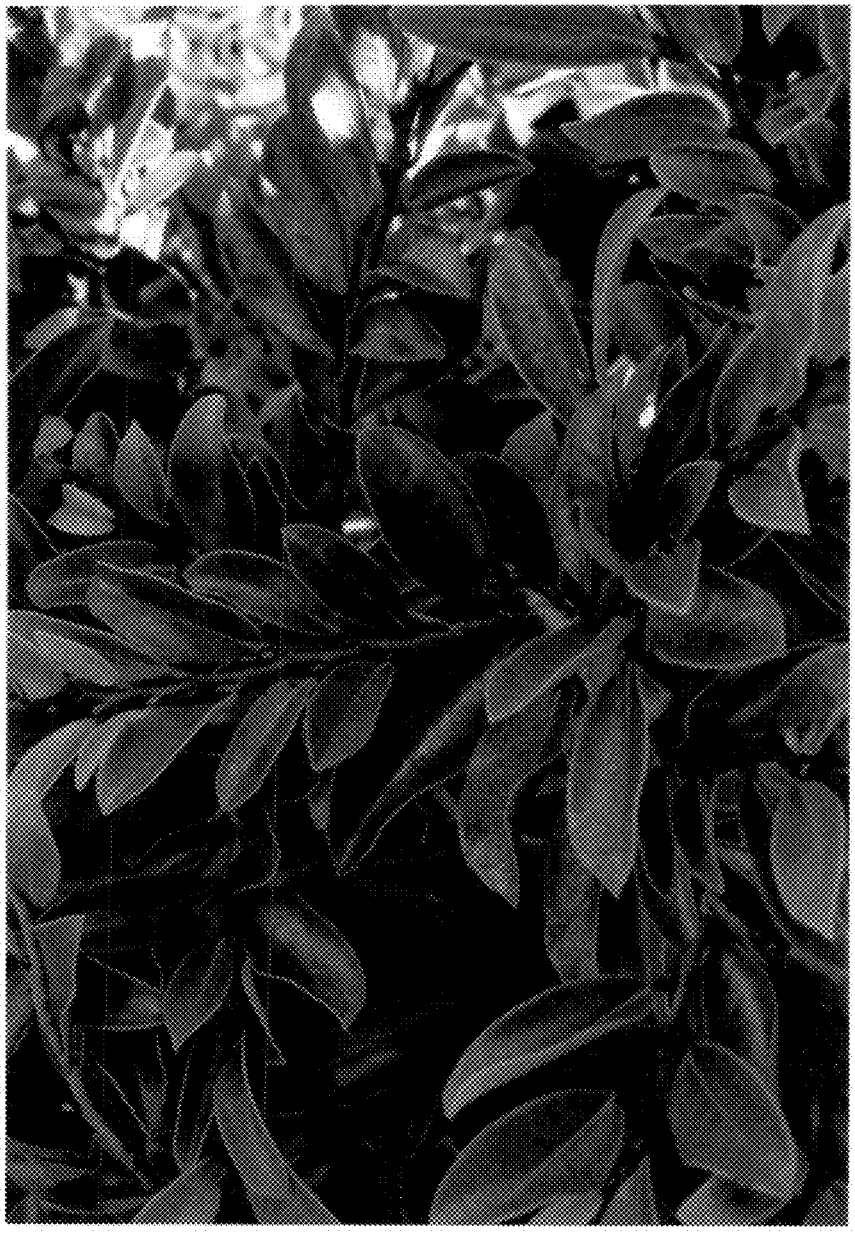
FIG. 2 illustrates a close-up of the mature foliage of a two-year-old 'CG-46-22' plant in the ground.
Figure 3:
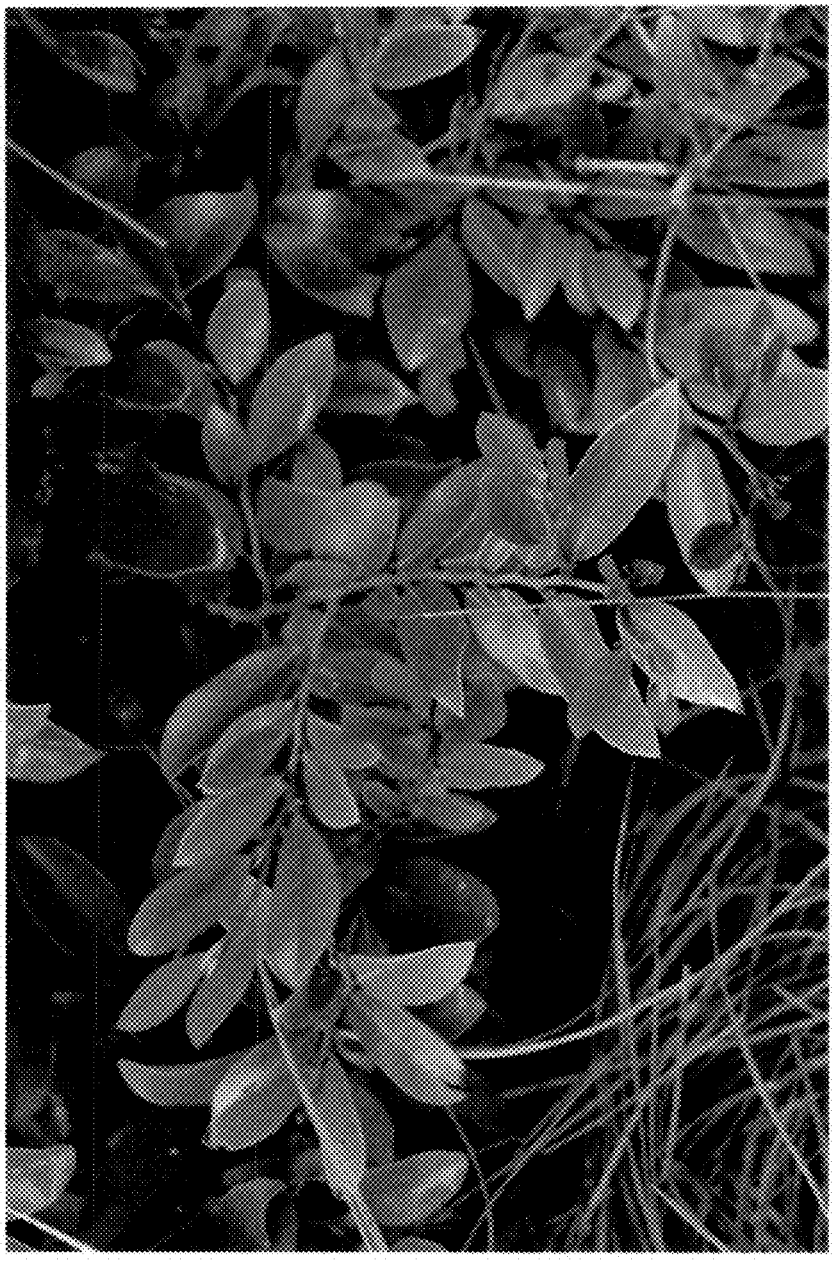
FIG. 3 illustrates the Greyed-Purple new growth.

In the following description, color references are made to The Royal Horticultural Society Colour Chart, 2015 Edition, except where general terms of ordinary dictionary significance are used. Plants for the description were grown in a 26.49-liter container under outdoor conditions in Watkinsville, GA. Plants were about two years old when the description was recorded.

Botanical classification: *Distylium* 'CG-46-22'.

PROPAGATION

Type of propagation typically used: Vegetative stem cuttings.

Time to initiate roots: About 6 weeks at 32° C. in summer.

Number of days to produce a rooted plant: About 3 months at 32° C. in summer.

Root description: Medium, well-branched, diffuse, and extensive. Colored RHS Geyed-White 156A.

PLANT

Type of plant: Broadleaf evergreen shrub.

Age of plant described: 2 years old.

Container size of the plant described: 26.49 liters.

Growth habit: Compact, mounded, spreading. Freely branching; removal of the terminal bud enhances lateral branch development.

Height: 91 cm.

Plant spread: 86 cm.

First year stems:

*Length*.—About 15 cm.
*Diameter*.—About 2 mm.
*Shape*.—Round.
*Color*.—Emerging: RHS Greyed-Purple 187C. Mature: RHS Yellow-Green 144A. Lenticels: RHS Brown 199D.
*Pubescence*.—Fine.
*Strength*.—Flexible.

Second year stems:

*Length*.—47 cm.
*Diameter*.—4 mm or more.
*Shape*.—Round.
*Color*.—RHS Brown N199D.
*Pubescence*.—None; smooth.
*Strength*.—Flexible when young; less when mature.

Trunk/main stem diameter: About 3 cm at the soil line.

Trunk/main stem color: RHS Brown N199B.

Bark: Does not exfoliate, covered with many lenticels, Greyed-Orange 164B in color, about 1 mm in diameter.

Internode length: About 1 cm.

Vegetative buds:

*Arrangement*.—Alternate.
*Shape*.—Ovoid with fused, pubescent bud scales.
*Length*.—About 4 mm.
*Width*.—About 1 mm.
*Color*.—RHS Brown N199B.

FOLIAGE

Leaf:

*Arrangement*.—Alternate, simple.
*Average length*.—About 5.4 cm.
*Average width*.—About 2.5 cm.
*Shape of blade*.—Lanceolate.
*Apex*.—Acute.
*Base*.—Cuneate.
*Margin*.—Entire, occasionally undulating.
*Texture of top surface*.—Smooth, thick, leathery.
*Texture of bottom surface*.—Smooth, thick, leathery.
*Color*.—Young foliage upper side: RHS Greyed-Purple 187C. Young foliage under side: RHS Yellow-Green N144A with some hints of Greyed-Purple 187C. Fully expanded foliage upper side: RHS Yellow-Green 147A. Fully expanded foliage under side: RHS Yellow-Green 146B.
*Venation*.—Type: Pinnate. Color, upper side: RHS Yellow-Green 144C. Color, under side: RHS Yellow-Green 144C. Color, secondary: RHS Yellow-Green 146A.
*Petiole*.—Length: About 4 mm. Diameter: About 1 mm. Color: RHS Yellow-Green 144A, both surfaces. Pubescence: Fine, RHS Brown 199A in color.

FLOWER

Natural flowering season: Late winter, approximately January to February in Watkinsville, GA. Individual flowers are showy for approximately 1 week and are self-cleaning.

Flower type and habit: Apetalous flowers with pubescent, 5-parted calyx are borne on short racemes from the leaf axils.

Flower diameter: About 5 mm.

Flower height: About 6 mm.

Persistence: Self-Cleaning.

Fragrance: None.

Pedicels:

*Length*.—About 2 mm.

*Color*.—RHS Yellow-Green 146C with pubescence colored Greyed-Orange165A.

Peduncles:

*Length*.—About 1 cm.

*Color*.—RHS Yellow-Green 146C with pubescence colored Greyed-Orange165A.

REPRODUCTIVE ORGANS

Stamens:

*Number*.—7 to 10.

*Filament length*.—About 3 mm.

*Filament width*.—Less than 1 mm.

*Color*.—RHS Greyed-Purple 185A.

*Pollen*.—Amount: Moderate. Color: RHS Yellow-White 158D.

Pistil:

*Position*.—Superior.

*Length*.—Approximately 1.1 mm.

*Width*.—2 mm.

*Color*.—RHS Greyed-Red 178B.

*Style*.—Number: 2 per flower. Length: 3 mm. Color: RHS Yellow-Green 146B.

*Stigma*.—Number: 2 per pistil. Length: About 6 mm. Color: RHS Greyed-Red 178B. Ovary: Number: 2 per flower. Length: About 2 mm. Width: About 2 mm. Color: RHS Yellow-Green 146B.

OTHER CHARACTERISTICS

Temperature tolerance: Temperature tolerance within USDA Zones 6-9. High temperature tolerance of at least 95 degrees F.

Fruits and seeds: Not observed to date.

Disease/pest resistance: Disease and pest resistance: Not observed to be susceptible nor resistant to normal disease and pest of *Distylium*.

What is claimed is:

1. A new and distinct cultivar of *Distylium* plant named 'CG-46-22', substantially as illustrated and described herein.

* * * * *